(12) United States Patent
Wu et al.

(10) Patent No.: US 8,835,605 B2
(45) Date of Patent: *Sep. 16, 2014

(54) USES OF CANCER-TARGETING PEPTIDES IN CANCER DIAGNOSIS

(75) Inventors: Han-Chung Wu, Taipei (TW); Chien-Yu Chiu, Taipei (TW)

(73) Assignee: Academia Sinica, Taipei (TW)

( * ) Notice: Subject to any disclaimer, the term of this patent is extended or adjusted under 35 U.S.C. 154(b) by 353 days.

This patent is subject to a terminal disclaimer.

(21) Appl. No.: 13/201,753

(22) PCT Filed: Feb. 19, 2010

(86) PCT No.: PCT/US2010/024647
§ 371 (c)(1),
(2), (4) Date: Oct. 25, 2011

(87) PCT Pub. No.: WO2010/096604
PCT Pub. Date: Aug. 26, 2010

(65) Prior Publication Data
US 2012/0093721 A1    Apr. 19, 2012

Related U.S. Application Data

(60) Provisional application No. 61/153,725, filed on Feb. 19, 2009.

(51) Int. Cl.
*A61K 38/10* (2006.01)
*A61K 38/16* (2006.01)
*A61K 51/00* (2006.01)
*C07K 7/08* (2006.01)

(52) U.S. Cl.
CPC ............................... *C07K 7/08* (2013.01)
USPC ............................. 530/327; 424/1.69

(58) Field of Classification Search
USPC ............................. 530/327; 424/1.69
See application file for complete search history.

(56) References Cited

U.S. PATENT DOCUMENTS

| | | |
|---|---|---|
| 2001/0018058 A1 | 8/2001 | Reed et al. |
| 2004/0059098 A1 | 3/2004 | Tang et al. |
| 2004/0146862 A1 | 7/2004 | Mack et al. |
| 2005/0186610 A1 | 8/2005 | Lee et al. |

*Primary Examiner* — Amber D Steele
(74) *Attorney, Agent, or Firm* — Cesari and McKenna, LLP

(57) ABSTRACT

Cancer-targeting peptides and uses thereof in cancer diagnosis.

15 Claims, 2 Drawing Sheets

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial
<220> FEATURE:
<223> OTHER INFORMATION: Synthetic peptide

<400> SEQUENCE: 1

Gln Asn Ile Tyr Ala Gly Val Pro Met Ile Ser Phe
1               5                   10
```

```
<210> SEQ ID NO 2
<211> LENGTH: 12
<212> TYPE: PRT
<213> ORGANISM: Artificial
<220> FEATURE:
<223> OTHER INFORMATION: Synthetic peptide

<400> SEQUENCE: 2

Glu Ala Thr Asn Ser His Gly Ser Arg Thr Met Gly
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic peptide

<400> SEQUENCE: 3

Thr Val Ser Trp Ser Thr Thr Gly Arg Ile Pro Leu
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic peptide

<400> SEQUENCE: 4

Gln Leu Glu Phe Tyr Thr Gln Leu Ala His Leu Ile
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic peptide

<400> SEQUENCE: 5

Ser Met Asp Pro Phe Leu Phe Gln Leu Leu Gln Leu
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic peptide

<400> SEQUENCE: 6

Arg Leu Leu Asp Thr Asn Arg Pro Leu Leu Pro Tyr
1               5                   10
```

USES OF CANCER-TARGETING PEPTIDES IN CANCER DIAGNOSIS

RELATED APPLICATION

This application is the national phase application of International Application No. PCT/US2010/024647, filed on Feb. 19, 2010, which claims priority to U.S. Provisional Application No. 61/153,725, filed on Feb. 19, 2009, the content of which is hereby incorporated by reference in its entirety.

BACKGROUND OF THE INVENTION

Early diagnosis significantly improves efficacy of cancer therapy. The key to accomplishing this mission is to identify agents that specifically target cancer cells.

SUMMARY OF THE INVENTION

The present invention is based on the unexpected discovery that a number of peptides, including QNIYAGVPMISF (SEQ ID NO:1), EATNSHGSRTMG (SEQ ID NO:2), TVSWSTT-GRIPL (SEQ ID NO:3), QLEFYTQLAHLI (SEQ ID NO:4), and SMDPFLFQLLQL (SEQ ID NO:5), specifically bind to breast cancer cells, thereby facilitating breast cancer diagnosis.

Accordingly, one aspect of this invention features a cancer-targeting conjugate containing a reporting agent (e.g., a fluorescent agent or a radioactive agent) and a cancer-targeting peptide including one of the amino acid sequences SEQ ID NOs:1-5. The term "peptide" used herein refers to a polymer composed of up to 100 amino acid monomers via peptide bond linkage. The reporting agent can be either encapsulated in a microparticle (e.g., a liposome) or linked to the cancer-targeting peptide via a covalent bond, directly or indirectly. When a fluorescent agent is used, it can be a quantum dot.

Another aspect of the invention is a method for breast cancer diagnosis. This method includes (i) contacting any of the cancer-targeting conjugates described above with a tissue of a subject, the tissue being suspected of containing breast cancer cells, (ii) detecting a signal released from the reporting agent, and (iii) determining the presence or absence of breast cancer cells in the subject based on intensity of the signal. In one example, the diagnostic method of this invention is performed in vitro, i.e., examining presence of breast cancer cells in a biopsy sample from the subject. In another example, it is an in vivo imaging method, in which an effective amount of the cancer-targeting conjugate is administered to the subject. "An effective amount" as used herein refers to the amount of the conjugate sufficient for breast cancer imaging. Effective amounts vary, as recognized by those skilled in the art, depending on route of administration, manner of formulation, and choice of excipient.

Also within the scope of this invention is use of any of the conjugates described above for breast cancer diagnosis or in manufacturing a medicament for breast cancer diagnosis.

The details of one or more examples of the invention are set forth in the description below. Other features or advantages of the present invention will be apparent from the following detailed description of several embodiments, and also from the appended claims.

BRIEF DESCRIPTION OF THE DRAWINGS

The drawings are first described.

DETAILED DESCRIPTION OF THE INVENTION

Figure 1:
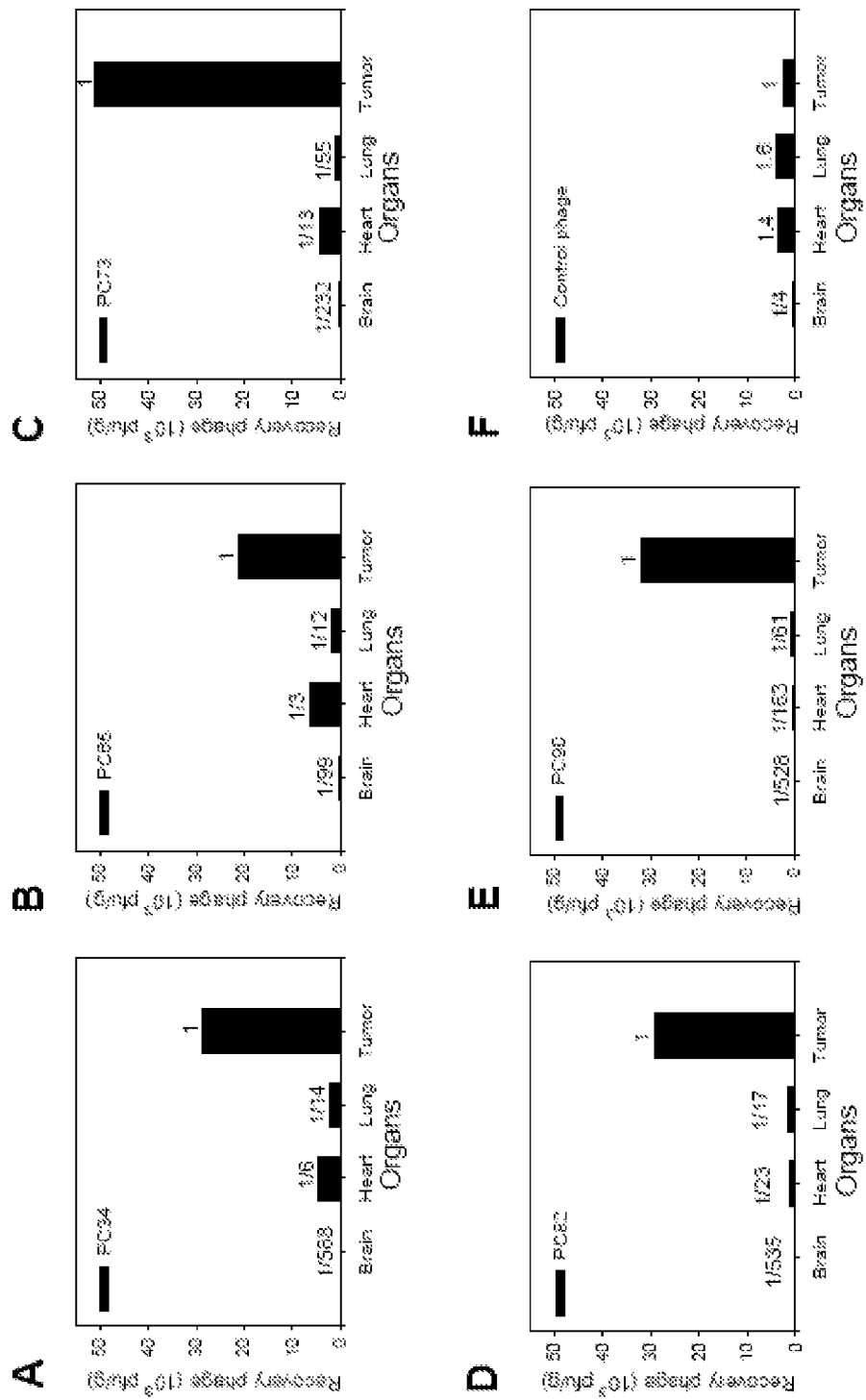
FIG. 1 is a diagram showing specific binding activities of cancer-targeting peptides, expressed on phage surfaces, to breast tumor xenografts. Panel A: phage clone PC34, displaying a peptide having the amino acid sequence of SEQ ID NO:1. Panel B: phage clone PC65, displaying a peptide having the amino acid sequence of SEQ ID NO:2. Panel C: phage clone PC73, displaying a peptide having the amino acid sequence of SEQ ID NO:3. Panel D: phage clone PC83, displaying a peptide having the amino acid sequence of SEQ ID NO:4. Panel E: phage clone PC90, displaying a peptide having the amino acid sequence of SEQ ID NO:5. Panel F: control phage clone PC34, displaying a control peptide.

The present invention relates to a number of breast cancer-targeting peptides, i.e., a peptide including one of the amino acid sequences of SEQ ID NOs:1-5. Each of the breast cancer-targeting peptides described herein can include up to 50 (e.g., 30) amino acids. These peptides can be prepared by conventional methods, i.e., chemical synthesis, or recombinant technology.

When necessary, any of the breast cancer-targeting peptides described herein can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2,4,6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

As shown in Examples 1-3 below, the breast cancer-targeting peptides described herein particularly bind to breast cancer tissues/cells, both in vitro and in vivo. Thus, when conjugated with a reporting agent (e.g., a fluorescent or radioactive agent in bioimaging), they direct the agent to a breast cancer site, thereby facilitating breast cancer diagnosis (both in vivo and in vitro). As used in this disclosure, "conjugated" means two entities (here a breast cancer targeting peptide and a reporting agent or an anti-breast cancer drug) are associated with sufficient affinity that the therapeutic/diagnostic benefit of the association between the two entities is realized. Conjugation can be achieved by covalent or noncovalent bonding, as well as by other forms of association, such as entrapment of one entity on or within the other, or of either or both entities on or within a third entity (e.g., a micelle).

In one example, one of the breast cancer-targeting peptides described herein is conjugated with a tumor-imaging agent, i.e., a radioactive molecule, a radiopharmaceutical, or an iron oxide particle (e.g., a quantum dot), to form an imaging conjugate that is used for in vivo breast tumor imaging. Radioactive molecules suitable for in vivo imaging include, but are not limited to, $^{122}$I, $^{123}$I, $^{124}$I, $^{125}$I, $^{131}$I, $^{18}$F, $^{75}$Br, $^{76}$Br, $^{76}$Br, $^{77}$Br, $^{211}$At, $^{225}$Ac, $^{177}$Lu, $^{153}$Sm, $^{186}$Re, $^{188}$Re, $^{67}$Cu, $^{213}$Bi, $^{212}$Bi, $^{212}$Pb, and $^{67}$Ga. Exemplary radiopharmaceuticals suitable for in vivo imaging include $^{111}$In Oxyquinoline, $^{131}$I Sodium iodide, $^{99m}$Tc Mebrofenin, and $^{99m}$Tc Red Blood Cells, $^{123}$I Sodium iodide, $^{99m}$Tc Exametazime, $^{99m}$Tc Macroaggregate Albumin, $^{99m}$Tc Medronate, $^{99m}$Tc Mertiatide, $^{99m}$Tc Oxidronate, $^{99m}$Tc Pentetate, $^{99m}$Tc Pertechnetate, $^{99m}$Tc Sestamibi, $^{99m}$Tc Sulfur Colloid, $^{99m}$Tc Tetrofosmin, Thallium-201, and Xenon-133. Fluorescent quantum dots known in the art, e.g., Qdot 800 ITK (Invitrogen, CA, USA), and CdSe QD (Nanoco, Manchester, UK) can also be used as the cancer imaging agent.

In any of the imaging conjugates described above, the breast cancer-targeting peptide can be linked via a covalent bond, directly or indirectly, to an imaging agent via methods known in the art. Alternatively, the breast cancer-targeting peptide is linked to a vehicle molecule (i.e., a microparticle), which encapsulates the imaging molecule/anti-breast cancer drug. Vehicle molecules include micelle, liposome (e.g., cationic liposome), nanoparticle, microsphere, or biodegradable polymer. A breast cancer-targeting peptide can be tethered to the vehicle molecule by a variety of linkages (e.g., a disulfide linkage, an acid labile linkage, a peptide-based linkage, an oxyamino linkage, or a hydrazine linkage). The imaging agent encapsulated within the vehicle can be associated with lipophilic molecules, which can aid in the delivery of the imaging agent to the interior of the vehicle.

In a preferred example, a breast cancer-targeting peptide is linked to a liposome that encapsulates a compound (e.g., a radioactive molecule or a fluorescent dye) to be delivered to a tumor site. The term "liposome" refers to vesicles comprised of one or more concentrically ordered lipid bilayers, which encapsulate an aqueous phase. The aqueous phase typically contains the compound to be delivered to a tumor site. Upon reaching a tumor site, the liposome fuses with the plasma membranes of local tumor cells or tumor blood vessel cells, thereby releasing the compound into the cytosol. Alternatively, the liposome is endocytosed or otherwise taken in by the tumor cells or of tumor blood vessel cells as the content of a transport vesicle (e.g., an endosome or phagosome). Once in the transport vesicle, the liposome either degrades or fuses with the membrane of the vesicle and releases its contents. Liposome membranes can be constructed so that they become destabilized when the nearby environment becomes acidic (see, e.g., PNAS 84:7851, 1987; Biochemistry 28:908, 1989). When liposomes enter a target cell, they become destabilized and release their encapsulated contents. This destabilization is termed fusogenesis. Dioleoylphosphatidylethanolamine (DOPE) is commonly used to facilitate this process.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

Any of the breast cancer imaging conjugates described herein can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

To use any of the conjugates described herein for tumor diagnosis, the conjugate can be administered parenterally, topically, rectally, nasally, buccally, vaginally, via an implanted reservoir, or via inhalation spray. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

Example 1

Binding of Cancer-Targeting Peptides Expressed on Surface of Phage Particles

BT483 cells (breast cancer cells) and human mucosal epithelial cells (normal cells) were seeded in a 96-well plate, following the procedures described in Lo et al., Mol. Cancer. Ther 7:579-589 (2008) and Lee et al., Cancer Res. 64:8002-8008 (2004). These cells were incubated with both a control helper phage that is inactivated by ultraviolet and one of the five test phages listed below, each expressing one of the five peptides also listed below:

| Phage Clones | Peptide Displayed |
|---|---|
| PC34: | QNIYAGVPMISF (SEQ ID NO: 1) |
| PC65: | EATNSHGSRTMG (SEQ ID NO: 2) |
| PC73: | TVSWSTTGRIPL (SEQ ID NO: 3) |
| PC82: | QLEFYTQLAHLI (SEQ ID NO: 4) |
| PC90: | SMDPFLFQLLQL (SEQ ID NO: 5) |

After several rounds of wash to remove unbound phage particles, the cells were further incubated with horseradish peroxidase (HRP) conjugated anti-M13 monoclonal antibody (Pharmacia, Uppsala, Sweden) and then with o-phenylenediamine dihydrochloride (sigma, MO, USA), a substrate of peroxidase. The cells were washed again and analyzed in an ELISA reader to measure the optical density at 490 nm in each well. The $OD_{490}$ values indicate the binding activity of the test phages to the breast cancer cells and to the normal cells. All of the five test phages exhibited significantly higher binding activities to the breast cancer cells than to the normal cells, indicating that the five peptides expressed thereon target cancer cells but not normal cells.

The binding activities of the five test phages to the breast cancer cells and to the normal cells were also determined by flow cytometry as follows. The cells were harvested and suspended in PBS containing 50 mM EDTA and then incubated with one of the five test phages. After washing, the cells were incubated with the anti-M13 antibody mentioned above and then with a FITC-conjugated goat anti-mouse IgG antibody. The cells were washed again and analyzed by a flow cytometer (Becton Dickinson). The results thus obtained show that the percentages of the test phage-bound cancer cells were significantly higher than those of the test phage-bound normal cells, indicating that all of the five peptides expressed on the test phages specifically bound to breast cancer cells.

Example 2

In Vivo Binding Activity of Test Phages to Cancer Tissues

SCID mice were injected subcutaneously (s.c.) in the dorsolateral flank with $1\times10^7$ BT483 cells to induce breast cancer xenografts. The mice bearing xenograft tumors at a size of around 300 mm³ were administered intravenously (i.v.) with one of the five test phages mentioned in Example 1 above ($10^9$ pfu) or a control phage. After perfusion, xenograft tumors and organs (i.e., brain, heart, and lung) were removed from each mouse and homogenized. The phages bound to each tissue sample were eluted, recovered using ER2738 bacterial cells as the host, and titered on IPTG/X-Gal agar plates, following the methods described in Lee et al., Cancer Res. 67:10958-10965 (2007) and Lo et al., Mol. Cancer. Ther 7:579-589 (2008).

As shown in FIG. 1, the recovery rates of phage clones PC34, PC65, PC73, PC82 and PC90 from tumor tissues were much higher than those from normal organs, including the brain, heart, and lung, indicating that all of the five phage clones homed to tumor mass, but not normal organs. More specifically, the concentrations of the phages homed to the tumor mass were 3.0 to 588 fold higher that those of the phages homed to the normal organs. The control phage targeted neither the tumor xenografts nor the normal organs.

Example 3

Cancer Targeting Activity of Peptide SMDPFLFQLLQL (SEQ ID NO:5)

The ability of phage clone PC90, expressing peptide SMDPFLFQLLQL (SEQ ID NO:5) for detecting presence of breast cancer cells in patient biopsy samples was tested as follows.

Fresh breast cancer tissue samples were obtained from twenty patients having mammary infiltrating ducal carcinoma. Each of the tissue samples was sliced to 4 μm and fixed in 1% paraformaldehyde. The sliced tissue samples were then incubated with PC90 or a control phage. After being washed by PBS containing 1% Tween 20 ($PBST_{0.1}$), the samples were incubated with an anti-M13 mouse mAb (Amersham Biosciences, Piscataway, N.J., USA) for 1 hour at room temperature, washed again with $PBST_{0.1}$, and the immunoreactivity of each sample was determined using a biotin-free super sensitive polymer-HRP detection system (Biogenex, San Ramon, Calif., USA), following the procedures described in Lee et al. (2004) and Lo et al. The slides, to which the tissue samples were attached, were counterstained with hematoxylin, mounted with Aquatex (Merck, Dannstadt, Germany), and examined by light microscopy. The percentage of the positively stained cells was determined following a method described in Hall et al., J. Pathol. 172:1-4 (1994). The results thus obtained show that 18 out of the 20 patients were determined as carrying breast cancer cells, using PC90 as a diagnosing agent, while no breast cancer cells were detected using the control clone.

The cancer targeting activity of PC90 was confirmed by a peptide competition assay, in which the cancer tissue samples were incubated with (1) the synthetic peptide (100 ng/ml) SMDPFLFQLLQL (SEQ ID NO:5) (SP90) and PC90 ($10^9$ pfu) or (2) the control peptide (100 ng/ml) RLLDTNRPLLPY (SEQ ID NO:6; see Lee et al., Cancer Res. 64:8002-8008, 2004) and PC90. SP90 and the control peptide were synthesized and purified by reverse-phase high-performance liquid chromatography. The resultant peptides, having a purity of greater than 95%, were conjugated, if necessary, with FITC or biotin at their N-termini.

The results obtained from this study showed that SP90, but not the control peptide, competed against PC90 for binding to the cancer cells in the tissue samples.

Next, the in vivo cancer targeting activity of PC90 was tested in breast tumor-bearing SCID mice following the method described in Example 2 above. The results showed that PC90 particles were bound to cancer cells in the tumor xenografts but not to normal organs, including the brain, heart, and lung.

SP90 was co-administered to test its ability of blocking PC90 from binding to the tumor tissues. Briefly, 100 µg SP90 or the control peptides described above were co-injected with PC90 to mice bearing breast tumor xenografts. The normal organs and tumor tissues were removed and fixed in Bouin's solution (Sigma, Mo., USA). After fixation, the samples were embedded in paraffin blocks, sliced to sections, and the sections were deparaffinized, rehydrated, and subjected to immunostaining using the mouse anti-M13 mAb described in Example 1 above. SP90 significantly inhibited PC90 from binding to tumor tissues. More specifically, 100 µg SP90 inhibited 97% of PC90 from binding to the tumor tissues while the control peptide did not exhibit any inhibitory activity.

Taken together, the results discussed above indicate that peptide SMDPFLFQLLQL (SEQ ID NO:5), either in synthetic form or being expressed on the surface of a phage, specifically target breast cancer cells.

Example 4

In Vitro Imaging of Breast Cancer Cells Using Peptide SP90 Conjugated with a Fluorescent Dye Peptide-conjugated liposomes containing fluorescent dye SRB were prepared as described in Lee et al. (2007), Lo et al, and Lee et al. (2004). Briefly, the peptide was coupled to NHS-PEG-DSPE [N-hydroxysuccinimido-carboxyl-polyethylene glycol (MW, 3400)-derived distearoylphosphatidyl ethanolamine] (NOF Corporation, Japan) in a 1:1.5 molar ratio. The reaction was completed and confirmed by quantifying the non-reacted amino groups using TNBS (Trinitrobenzenesulfonate) (Sigma, Mo., USA). SRB was encapsulated by liposomes at a ratio of 1 mg of the dye per 10 µmol phospholipids. Peptidyl-PEG-DSPE was then conjugated to the SRB-encapsulated liposomes after co-incubation at a transition temperature of the lipid bilayer. Following this method, a SP90-conjugated liposome encapsulating SRB ("SP90-LS") and a control peptide-conjugated liposome encapsulating SRB ("CP-LS") were prepared.

BT483 cells were incubated at 37° C. with SP90-LS, CP-LS, or SRB-encapsulated liposomes ("LS") for five minutes. The cells were then washed with PBS, stained with DAPI, and then examined a Leica confocal microscope (TCS-SP5-AOBS) to determine localization of SRB and DAPI in the cells. No fluorescent signal was detected in the cells incubated with LS and CP-LS, while a strong fluorescent signal was detected in the cell incubated with SP90-LS. This data indicates that SP90 specifically targeted breast cancer cells, resulting in endocytosis of the SRB-encapsulated liposomes conjugated to it.

Example 5

In Vivo Tumor Imaging Using SP90 Conjugated with a Quantum Dot

Thiolated SP90 was conjugated with Qdot 800 ITK amino PEG quantum dots (QD800; Invitrogen, CA, USA) via a linker Sulfosuccinimidyl-4-(N-maleimidomethyl)cyclohexane-1-carboxylate (sulfo-SMCC, Pierce, Ill., USA) to produce a fluorescent probe SP-QD.

SCID female mice, 6-week old, were subcutaneously implanted with $5 \times 10^6$ BT483 cell at their dorsolateral flank to induce breast cancer xenografts. The tumor volumes in these mice were determined by the formula: length$\times$(width)$^2 \times 0.52$.

Figure 2:
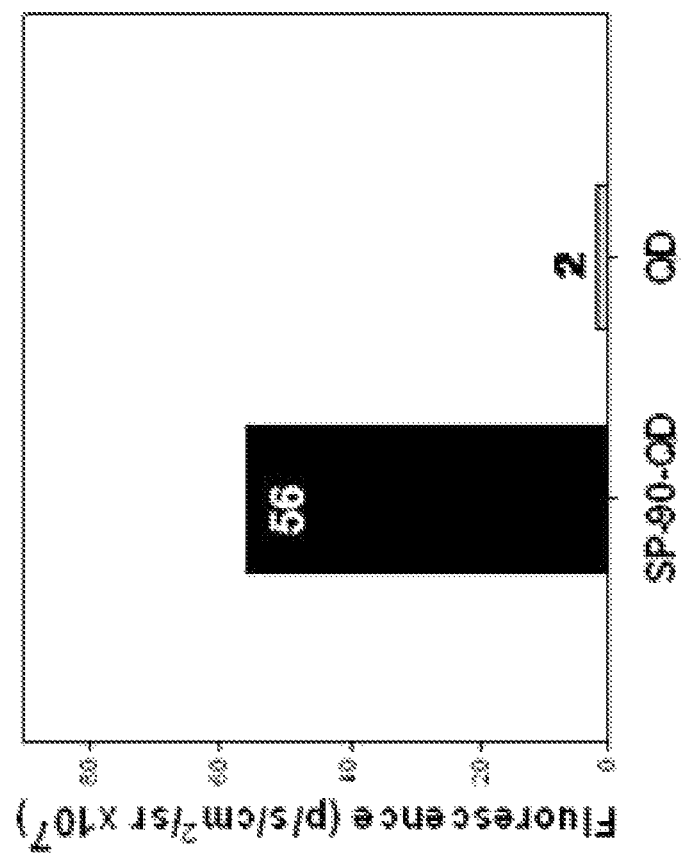
FIG. 2 is a chart showing fluorescent levels in breast xenografts in SCID mice treated with quantum dots-conjugated cancer-targeting peptide SP90 (SEQ ID NO:5).

The mice bearing xenograft tumors at a size of around 50-100 mm$^3$ were randomly assigned to two groups, each of which was injected i.v. with 200 pmol SP-QD or free Qdot 800 ITK amino PEG quantum dots (QD). Fifteen minutes later, the mice were anethetized by isofluoran and examined with a Xenogen IVIS 200 imaging system (excitation: 430/30 nm; emission: 730/30 nm) to determine fluorescent intensities at their tumor sites. The results thus obtained were normalized against background fluorescent intensities using the Living image software 9Xenogen, MA, USA). As shown in FIG. 2, the tumor site fluorescent intensity in the mice treated with SP-QD was around 28-fold of that in the mice treated with QD. This result demonstrates that SP-90 is useful in breast cancer in vivo imaging.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A conjugate for diagnosing or imaging breast cancer, comprising a reporting agent and a breast cancer-targeting peptide linked to the reporting agent, wherein the peptide contains the sequence of QNIYAGVPMISF (SEQ ID NO:1), EATNSHGSRTMG (SEQ ID NO:2), TVSWSTTGRIPL (SEQ ID NO:3), QLEFYTQLAHLI (SEQ ID NO:4), or SMDPFLFQLLQL (SEQ ID NO:5), the peptide having 12 to 50 amino acid residues.

2. The conjugate of claim 1, wherein the peptide has the sequence of SEQ ID NO:5.

3. The conjugate of claim 2, wherein the peptide consists of the sequence of SEQ ID NO:5.

4. The conjugate of claim 2, wherein the reporting agent is a fluorescent agent or a radioactive agent.

5. The conjugate of claim 4, wherein the fluorescent agent is a quantum dot.

6. The conjugate of claim 4, wherein the reporting agent is encapsulated inside a microparticle.

7. The conjugate of claim 6, wherein the microparticle is a liposome.

8. The conjugate of claim 3, wherein the reporting agent is a fluorescent agent or a radioactive agent.

9. The conjugate of claim 8, wherein the fluorescent agent is a quantum dot.

10. The conjugate of claim 8, wherein the reporting agent is encapsulated inside a microparticle.

11. The conjugate of claim 10, wherein the microparticle is a liposome.

12. The conjugate of claim 1, wherein the reporting agent is linked to the cancer targeting peptide via a covalent bond.

13. A method for diagnosing breast cancer in vitro, comprising:
   contacting a tissue of a subject with the conjugate of claim 1, wherein the tissue is suspected of containing breast cancer cells;
   detecting a signal released from the reporting agent, and
   determining the presence or absence of breast cancer in the subject based on intensity of the signal.

14. The method of claim 13, wherein the peptide has the sequence of SEQ ID NO:5.

15. The method of claim 14, wherein the peptide consists of the sequence of SEQ ID NO:5.

* * * * *